United States Patent
Reusch et al.

(10) Patent No.: US 7,115,787 B2
(45) Date of Patent: Oct. 3, 2006

(54) METHOD FOR PRODUCING TERT-BUTANOL BY MEANS OF REACTIVE RECTIFICATION

(75) Inventors: Dieter Reusch, Marl (DE); Andreas Beckmann, Recklinghausen (DE); Franz Nierlich, Marl (DE); Axel Tuchlenski, Weinheim (DE)

(73) Assignee: OXENO Olefinchemie GmbH, Marl (DE)

( * ) Notice: Subject to any disclaimer, the term of this patent is extended or adjusted under 35 U.S.C. 154(b) by 14 days.

(21) Appl. No.: 10/534,973

(22) PCT Filed: Nov. 11, 2003

(86) PCT No.: PCT/EP03/12535

§ 371 (c)(1),
(2), (4) Date: May 16, 2005

(87) PCT Pub. No.: WO2004/058669

PCT Pub. Date: Jul. 15, 2004

(65) Prior Publication Data

US 2006/0025638 A1     Feb. 2, 2006

(30) Foreign Application Priority Data

Dec. 24, 2002    (DE)  ................ 102 60 991

(51) Int. Cl.
*C07C 29/04*     (2006.01)
*C07C 29/03*     (2006.01)

(52) U.S. Cl. ............. 568/895; 568/896; 568/897; 568/898; 568/899; 568/900; 568/901

(58) Field of Classification Search ........... 568/895, 568/896, 897, 898, 899, 900, 901
See application file for complete search history.

(56) References Cited

U.S. PATENT DOCUMENTS

| | | |
|---|---|---|
| 5,258,560 A | 11/1993 | Marker |
| 5,518,699 A | 5/1996 | Kashnitz et al. |
| 2004/0171891 A1 | 9/2004 | Scholz et al. |
| 2005/0014985 A1 | 1/2005 | Grund et al. |
| 2005/0043571 A1 | 2/2005 | Fernandez et al. |

FOREIGN PATENT DOCUMENTS

| | | |
|---|---|---|
| EP | 0 415 310 | 3/1991 |
| EP | 0 466 954 | 1/1992 |

OTHER PUBLICATIONS

U.S. Appl. No. 10/526,763, filed Mar. 7, 2005, Reusch, et al.

*Primary Examiner*—Elvis O. Price
(74) *Attorney, Agent, or Firm*—Oblon, Spivak, McClelland, Maier & Neustadt, P.C.

(57) ABSTRACT

The invention relates to a process for preparing tert-butanol (TBA) from isobutene-containing mixtures, in which at least part of the conversion is achieved with the aid of a reactive rectification.

10 Claims, 3 Drawing Sheets

METHOD FOR PRODUCING TERT-BUTANOL BY MEANS OF REACTIVE RECTIFICATION

The invention relates to a process for preparing tert-butanol (TBA) from isobutene-containing mixtures with the aid of a reactive rectification.

tert-Butanol (TBA) is an important industrially produced product and is used as solvent and as intermediate for the preparation of methyl methacrylate. It is a precursor for the preparation of peroxides such as peroxyketals, peresters or dialkyl peroxides having at least one tertiary butyl group. These compounds are used as oxidants and as initiators for free-radical reactions, for example olefin polymerization or crosslinking of polymers. As an intermediate, tert-butanol is used for isolating pure isobutene from isobutene mixtures. Furthermore, it is a reagent for introduction of tertiary butyl groups. Its alkali metal salts are strong bases which are employed in many syntheses.

TBA can be prepared by oxidation of isobutane or is obtained as coproduct in the epoxidation of olefins using tert-butyl peroxide. Such processes are usually carried out in the liquid phase and can be divided into two groups: a) processes in which the reaction occurs in an aqueous catalyst solution and b) heterogeneous catalytic processes in which solid catalysts which are insoluble in the reaction phase are used.

Homogeneous catalytic processes employ sulfuric acid, heteropolyacids, p-toluenesulfonic acid or other strong acids as catalysts. These high-activity catalysts usually form a homogeneous phase with the reaction product, so that the catalyst cannot be removed by mechanical means. If the tertiary butanol is isolated from the reaction solution by distillation, the yield is reduced by backreaction and the formation of by-products.

The hydration of isobutene to form tert-butanol with the aid of solid, acidic catalysts which are soluble neither in the starting materials nor in the products has the advantage that the reaction mixture is acid-free and can be worked up to obtain tert-butanol without losses due to redissociation or other secondary reactions. The reaction occurs at the surface of the catalyst. For a reaction to take place, both reactants must be present at the active site on the catalyst at the same time. This is made difficult by water and isobutene or an isobutene-containing hydrocarbon mixture not being miscible with one another. To obtain acceptable conversions, use is frequently made of solvents which make it possible to obtain a homogeneous mixture of water and the isobutene feed mixture.

DE 30 31 702 describes, for this purpose, the use of methanol as solvent both for water and for isobutene or an isobutene-containing hydrocarbon mixture. tert-Butanol and methyl tert-butyl ether are obtained together as products. A disadvantage of this process is that the solvent has to be separated off again from the desired product in an addition separation unit and therefore incurs additional apparatus costs and operating costs.

In EP 0 010 993, aliphatic carboxylic acids having from 1 to 6 carbon atoms are used as solvents for both starting materials. The tertiary butyl esters of these acids are formed as by-products. These have to be hydrolyzed to tert-butanol and carboxylic acids. Here too, it is a disadvantage that the solvent has to be separated off again from the desired product in an additional separation unit and additional apparatus costs and operating costs are therefore incurred.

WO 99/33775 describes a process for preparing tert-butanol by reaction of a mixture comprising water, tert-butanol and isobutene or an isobutene-containing hydrocarbon mixture over a cation-exchange resin in a multistage series reactor. The reaction temperature in the individual reactors is below 65° C. Part of the intermediate is recirculated from the first reactor to the inlet of the same reactor. The circulation rate (amount of intermediate mixture which is recirculated to the first reactor, as a ratio to the feed mixture) is from 1.8 to 10 and the proportion by weight of tert-butyl alcohol based on the hydrocarbon mixture (total of isobutene and any other hydrocarbons) at the inlet of the first reactor is from 0.5 to 3.5. The mixture from the first reactor which is not recirculated flows without intermediate introduction of water through two further reactors in a single pass. The crude product from the last reactor is worked up by distillation. If desired, part of the tert-butanol obtained is recirculated to the first reactor. A disadvantage of this process is the low space-time yield.

DE 030 25 262 and U.S. Pat. No. 6,111,148 disclose processes for preparing TBA from isobutene and water, in which the target product, viz. tert-butanol, is used as solubilizer for isobutene and water. In this process, a mixture of isobutene or an isobutene-containing hydrocarbon mixture, water and tert-butanol is converted into tert-butanol over a strongly acidic ion-exchange resin in a plurality of reactors connected in series. The reaction mixture leaving the last reactor is distilled. As top product, a mixture of unreacted isobutene and any hydrocarbons from the feed which are inert under the reaction conditions are obtained. An aqueous tert-butanol solution is obtained as bottom product. Part thereof is recirculated to the first reactor.

All the processes mentioned have the disadvantage that complete conversion of isobutene to TBA is not possible because of the position of the thermodynamic equilibrium. Accordingly, it is also not possible to remove isobutene completely from an isobutene-containing $C_4$-hydrocarbon fraction, e.g. raffinate I. Furthermore, conventional processes have the disadvantage that the rection has to be carried out at low temperatures in order to shift the position of the equilibrium in the direction of TBA. This results in slow reaction rates and thus large reactor volumes.

To overcome reaction equilibria, the concept of reactive distillation has been found to be useful in numerous industrially important reactions. Examples which may be mentioned are ether syntheses (methyl tert-butyl ether (MTBE), ethyl tert-butyl ether (ETBE), methyl tert-pentyl ether (TAME), ethyl tert-pentyl ether (TAEE)), esterifications, transesterifications, isomerizations, ether cleavages and dehydrations. The principle of reactive distillation is based on the distillation occurring in parallel to the reaction. The reaction products are selectively taken off from the reaction zone and thus removed from the equilibrium.

The preparation of tertiary alcohols, in particular tertiary amyl alcohol (tert-pentanol) and tertiary butyl alcohol, by reactive distillation in the presence of an acidic ion exchanger is described in EP-A-0 415 310 and DE 100 50 627. In EP-A-0 415 310, the process is carried out in a reactive distillation column provided with helically wound mesh structures. In DE 100 50 627, on the other hand, preference is given to using structured multipurpose packing elements as are, for example, commercially available as Katapak® from Sulzer AG or Montz Multipak from Montz GmbH. The column concept is the same in both processes, and the stripping section of the column is fitted exclusively with distillation internals while the enrichment section is preferably equipped with reactive internals. In both EP-A-0 415 310 and DE 100 50 627, the $C_4$-hydrocarbon mixture is fed in below the reactive zone, while the water is introduced into the column above the reactive zone. A disadvantage of this mode of operation is that demixing of organic and aqueous phase occurs, especially in the upper part of the column without the solubilizing action of the tertiary alcohol, and seriously restricts the effectiveness of the distillation and in particular the reaction, so that the space-time yield in the reactive distillation column is reduced. In addition, the reaction rate is reduced by hydration of the catalyst with water, since isobutene as a nonpolar compound can diffuse only slowly through the hydration shell.

DE 100 56 685 discloses a process for preparing isobutene from an isobutene- and n-butene-containing $C_4$ stream, in which a chemical reaction to form a downstream product of isobutene, e.g. MTBE, TBA or a carboxylic ester, is firstly carried out in a reactive distillation. This downstream product is purified in a distillation stage and subsequently redissociated to form isobutene in a second reactive distillation. In this process, the isobutene-containing $C_4$-hydrocarbon mixture is fed into the catalyst packing in the reactive distillation plant.

Since the known processes are not satisfactory in respect of the space-time yield in the reactive distillation column and/or the selectivity and/or the residual isobutene content in the remaining $C_4$ fraction, it is an object of the invention to develop a process which gives a higher space-time yield and virtually complete isobutene conversion.

It has now been found that the space-time yield for the formation of TBA from isobutene and water in the presence of an acid catalyst in a reactive distillation column and the isobutene conversion can be increased and the isobutene content of the distillate can be reduced if both the isobutene-containing mixture and water are fed in below the reaction zone.

EP 0 726 241 discloses a process for the dissociation of TBA into isobutene and water, i.e. the reverse reaction, by means of reactive distillation. Here too, the feed mixture is introduced into the reactive distillation column below the reaction zone. A TBA/isobutene/water mixture which, however, does not react to reform TBA but is converted virtually completely into isobutene and water is present in the reactive zone. Surprisingly, this reactor concept can also be used for the formation of TBA from water and isobutene.

The present invention accordingly provides a process for preparing tertiary butanol (TBA) by reacting an isobutene-containing $C_4$-hydrocarbon stream with water over a solid acidic catalyst wherein the isobutene-containing $C_4$-hydrocarbon stream and water are fed into a reactive distillation column below the reaction zone.

In one process variant, a mixture of an isobutene-containing $C_4$-hydrocarbon stream, water and TBA is fed into the reactive distillation column. This mixture can be obtained by reaction of an isobutene-containing $C_4$-hydrocarbon stream with water over a solid, acidic catalyst in a preliminary reactor.

The preliminary reaction of an isobutene-containing $C_4$-hydrocarbon stream with water over a solid acidic catalyst is preferably carried out to an isobutene conversion into tert-butanol of from 65 to 97% and the mixture obtained in this way is fed into the reactive distillation column.

In the process of the invention, introduction of the reaction mixture below the reaction packing is essential. Water and the isobutene-containing $C_4$-hydrocarbon stream can be fed into the reactive distillation column at the same point or at various points. For example, water can be introduced above the $C_4$-hydrocarbon.

Figure 1:
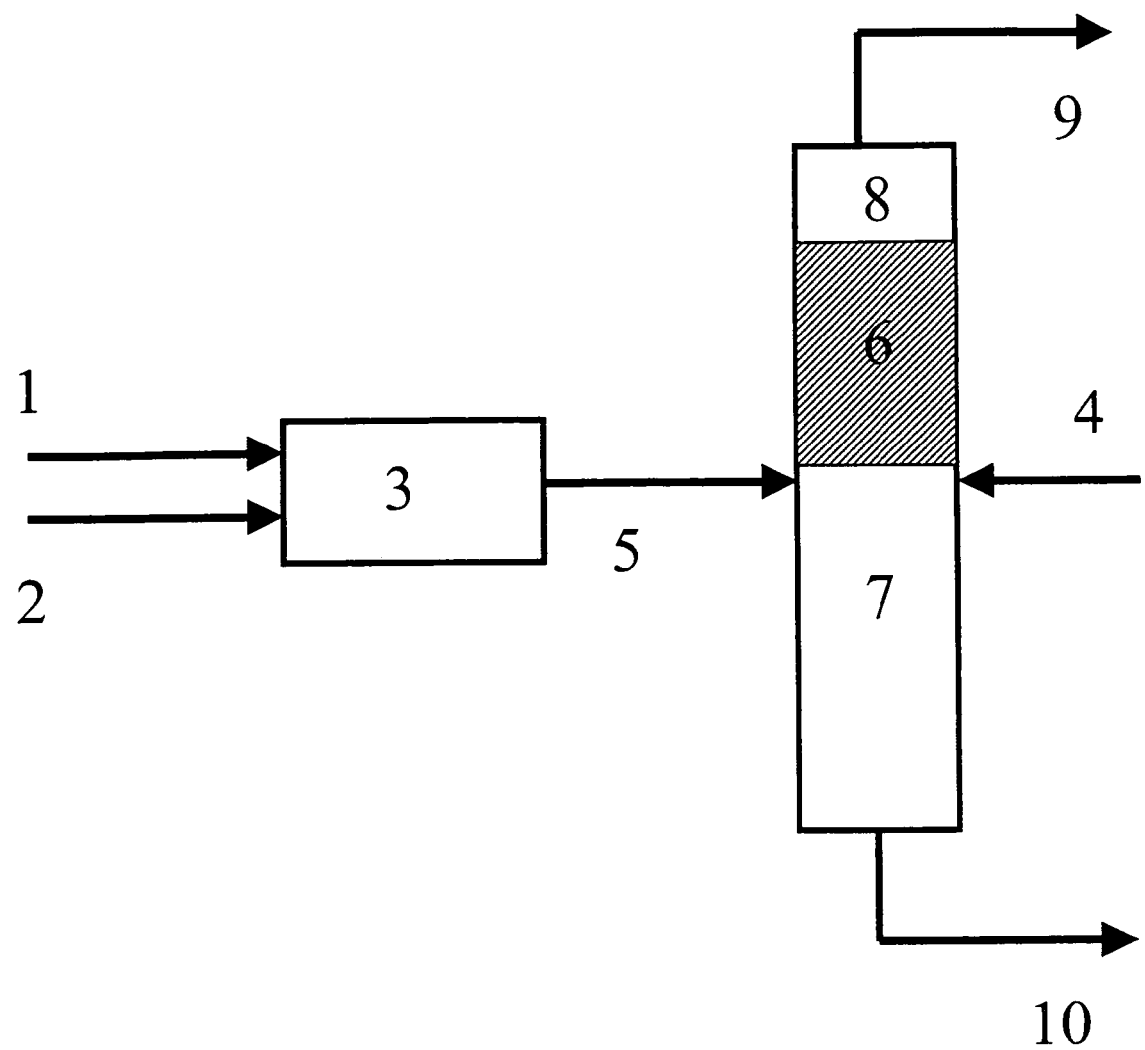
FIGS. 1–3 depict block diagrams of a plant in which TBA can be prepared by the process of the invention.

A block diagram of a plant in which TBA can be prepared by the process of the invention is shown in FIG. 1. The isobutene-containing $C_4$-hydrocarbon mixture (1) is fed together with water (2), which may contain TBA as solubilizer, into the reactors (3). The reactors (3) can comprise from 1 to 5 stages, preferably 3 or 4 stages. The prereacted mixture (5) can be fed together with an optional water stream (4) into the reactive rectification. The feed position for the optional water stream (4) is in the stripping section of the reactive rectification column. The water stream (4) is preferably introduced at the same height on the column as the prereacted mixture (5). In a particular embodiment of the process, additional water (4) can be added to the prereacted mixture (5) before it enters the reaction column. Above the saturation concentration, this can also lead to demixing to give an organic phase and an aqueous phase.

As an alternative, the preliminary reactor can be dispensed with and stream (1) and water (2 or 4) are fed directly into the reactive distillation column. The feed positions are located below the reactive region (6). A distillation region can be located between the feed point and the reaction zone. Below the reactive region, there is a pure distillation region which serves to separate off the TBA and any excess water. The bottom product (10) comprises predominantly TBA and water, ideally with water concentrations lower than in the water/TBA azeotrope. If desired, a further distillation region (8) having from 0 to 10 theoretical plates, preferably from 0 to 6 theoretical plates, can be located above the reactive region to adjust the isobutene concentration in the reaction zone. The top product (9) obtained is a $C_4$ mixture having low residual contents of isobutene and water.

Usual components such as pumps, compressors, valves and vaporizers are not shown in the block diagram but are of course components of a plant.

In the process of the invention, the reaction of isobutene with water to form TBA is preferably carried out in two stages (see FIG. 1). The first stage comprises the reaction of isobutene in the $C_4$ mixture with water, with or without addition of TBA as solubilizer, in one or more reactors, in the ideal case until the thermodynamic equilibrium between TBA, water and isobutene has been established in a homogeneous solution. The reactors of the first stage can be conventional fixed-bed reactors containing the same catalysts which are described below for the second stage. The reactors are usually operated at 30–110° C. and 5–50 bara.

Typical compositions of the reaction mixtures obtained are described in the examples. In general, these mixtures contain less than 20% by mass, in particular less than 15% by mass, of isobutene, which is converted very selectively into TBA in the subsequent second stage, viz. the reactive distillation column.

In the process variant with a preliminary reactor, in which the isobutene-containing stream is prepared by reacting an isobutene-containing $C_4$-hydrocarbon stream with water over an acidic catalyst, this can also be carried out to a limited conversion of from 65 to 97%. Preference is in this case given to isobutene conversions of from 75 to 97%, in particular from 80 to 96%, very particularly preferably from 82 to 95%.

This can be achieved, for example, by reacting an isobutene-containing $C_4$-hydrocarbon stream over an acidic fixed-bed catalyst in a plurality of reaction stages. Here, the reactors are connected in series and/or in parallel. The individual reactors are operated in a single pass or in a loop mode. The reaction product obtained from the preliminary reactor or preliminary reactor system is a mixture comprising the unreacted materials from the $C_4$-hydrocarbon stream, e.g. isobutane, n-butane, 1-butene and 2-butene, together with isobutene, tert-butanol and water. The concentrations of isobutene, tert-butanol and water in this stream are close to the thermodynamic equilibrium at the respective temperature at the reactor outlet.

As feeds to the process of the invention, it is possible to use $C_4$-hydrocarbon mixtures comprising both isobutene and linear butenes, but no acetylene derivatives and less than 8000 ppm by mass of butadiene. Industrial mixtures which may comprise both isobutene and linear butenes are, for example, light naphtha fractions from refineries, $C_4$ fractions from FCC units or steam crackers, mixtures from Fischer-Tropsch syntheses, mixtures from the dehydrogenation of butanes, mixtures from skeletal isomerization of linear butenes, mixtures formed by metathesis of olefins or other industrial processes.

These mixtures can be used in the process of the invention after removal of the multiply unsaturated compounds. For example, a suitable feed mixture can be obtained from the $C_4$ fraction from a steam cracker by extraction of the butadiene or selective hydrogenation thereof to linear butenes. This mixture (raffinate I or selectively hydrogenated cracking $C_4$) comprises n-butane, isobutane, the three linear butenes and isobutene and is a preferred starting material for the process of the invention.

If the isobutene-containing stream is fed together with water into the reactive distillation column below the reactive packing, the low-boiling $C_4$-hydrocarbons rise in vapor form into the reaction zone and, due to the minimum azeotrope of water and $C_4$-hydrocarbons, part of the water is also transported in vapor form together with the feed into the reaction zone. Any TBA present in the feed mixture and part of the water remain in the liquid phase and are discharged under level control.

When a $C_4$-hydrocarbon mixture, e.g. raffinate I, is used as feed, the $C_4$-hydrocarbons present in the azeotrope comprise isobutene, isobutane, n-butane, 1-butene and 2-butenes. Isobutene and water are reacted in the reactive zone of the column to form TBA, which flows as high boiler to the bottom of the column. The other constituents of the azeotrope do not react with water under the reaction conditions and are separated off as a water-containing azeotrope at the top of the column.

In the ideal case, the mixture separated off at the top of the reactive distillation column contains no or virtually no isobutene.

In a further process variant, the mixture obtained at the top of the reactive distillation column is separated into an aqueous phase and an organic phase and the aqueous phase is returned to the reactive distillation column.

This process variant has the advantage that the water of reaction is largely circulated and the product from the top of the column contains only small amounts of water.

If desired, part of the organic distillate phase or part of the total distillate can be recirculated to the reactive distillation column.

The recirculation of the aqueous distillate phase can take place above and/or below the reaction zone, while the organic distillate phase can be recirculated to above the reaction zone.

The reactive distillation column contains the catalyst in the enrichment section, and separation trays or distillation packing are/is present above and below the catalyst packing. The catalyst is either integrated into packing, for example KataMax® (EP 0 428 265), KataPak® (EP 0 396 650) or MultiPak® (Utility Model No. 298 7 007.3), or polymerized onto shaped bodies (U.S. Pat. No. 5,244,929). Preference is given to using catalytic packing having a high catalyst content, e.g. Katapak-SP 12 or, particularly preferably, Katapak-SP 11.

The term reactive distillation encompasses all process engineering measures in which distillation and reaction are carried out simultaneously. In the reactors described, this is achieved by a particular configuration of the packing in a column. In the process of the invention, it is also possible to separate these regions physically without losing the advantages of a reactive distillation.

In one process variant, the reactive distillation column is configured as a distillation column provided with one or more external reactors in which the catalyst is present and through which a secondary stream passes.

Figure 2:
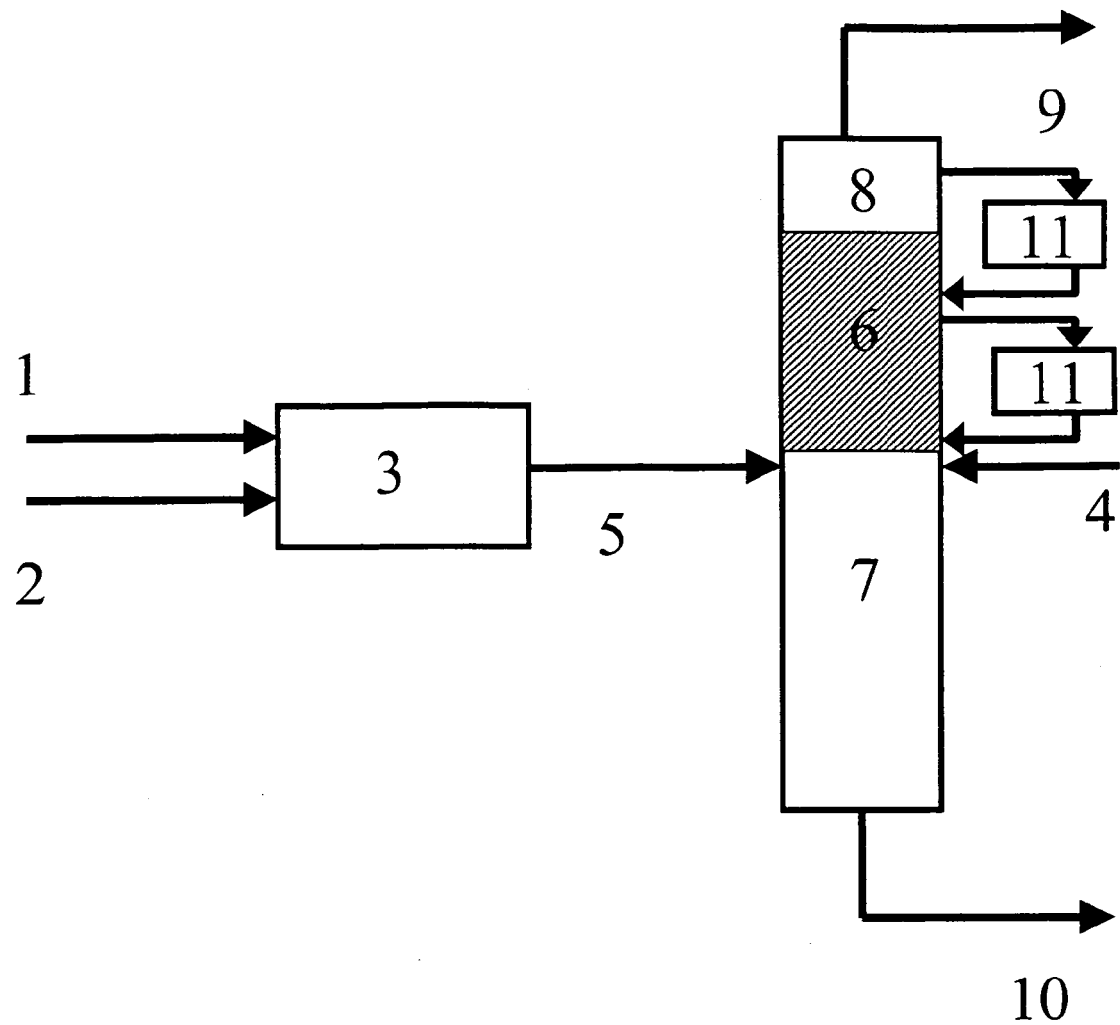

All or part of the catalyst can be installed in external reactors (11), as shown in FIG. 2. In this way, a larger amount of catalyst can be used and catalyst replacement is considerably simplified.

In a further variant, the reactive distillation column is configured as a distillation column provided with one or more catalyst-containing reactors integrated into the distillation section.

Figure 3:
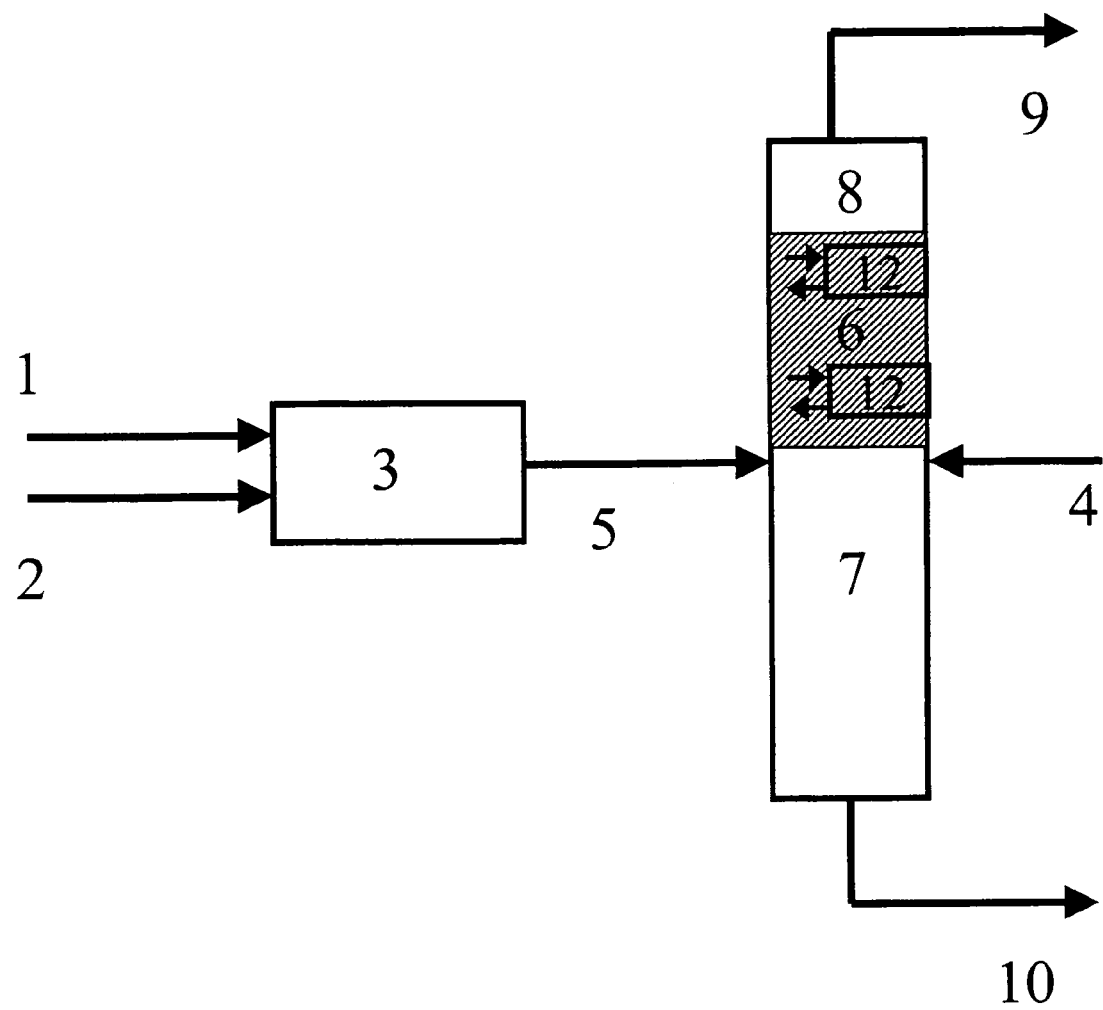

Here, all or part of the catalyst can be installed in integrated reactors (12), as shown in FIG. 3. An integrated reactor or integrated reaction stage is, for example, a catalyst bed through which only liquid phase flows and which thus makes intensive feed/catalyst contact possible. In terms of construction, this can be realized, for example, as in the Catacol process of IFP U.S. Pat. No. 5,776,320 or as a catalyst bed in downcomers of a distillation tray. A larger amount of catalyst can likewise be used in this way.

As actual catalyst, a solid which is soluble neither in the feed mixture nor in the product mixture and has acid centers on its surface is used in both stages of the process. Under the reaction conditions, the catalyst must release no acidic substances into the product mixture, because this would lead to losses in yield.

The activity of the catalysts has to be such that under the reaction conditions they catalyze the addition of water onto isobutene but barely the addition onto linear butenes. Furthermore, they must barely, if at all, catalyze the oligomerization of olefins.

A group of acidic catalysts which can be used in the process of the invention consists of solid ion-exchange resins having sulfonic acid groups. Suitable ion-exchange resins are, for example, ones which are prepared by sulfonation of phenol/aldehyde condensates or of cooligomers of aromatic vinyl compounds. Examples of aromatic vinyl compounds for preparing the cooligomers are: styrene, vinyltoluene, vinylnaphthalene, vinylethylbenzene, methylstyrene, vinylchlorobenzene, vinylxylene and divinylbenzene. In particular, the cooligomers formed by reaction of styrene with divinylbenzene are used as precursor for the preparation of ion-exchange resins having sulfonic acid groups. The resins can be in gel form, macroporous or of the sponge type. Strongly acidic resins of the styrene-divinylbenzene type are sold, for example, under the following trade names: Duolite C20, Duolite C26, Amberlyst 15, Amberlyst 35, Amberlite IR-120, Amberlite 200, Dowex 50, Lewatit SPC 118, Lewatit SPC 108, Lewatit K2621, Lewatit K2629, Lewatit K2431.

The properties of these resins, in particular specific surface area, porosity, stability, swelling or shrinkage and exchange capacity, can be varied via the production process.

The ion-exchange resins can be used in their H form in the process of the invention. Preference is given to using macroporous resins, for example Lewatit SCP 118, Lewatit SCP 108, Amberlyst 15 or Amberlyst 35, Lewatit K2621, Lewatit K2629, Lewatit K2431. The pore volume is from 0.3 to 0.9 ml/g, in particular from 0.5 to 0.9 ml/g. The particle size of the resin is from 0.3 mm to 1.5 mm, in particular from 0.5 mm to 1.0 mm. The particle size distribution can be relatively narrow or broad. Thus, for example, it is possible to use ion-exchange resins having a very uniform particle size (monodisperse resins). The acid capacity of the ion exchangers is, based on the form supplied, 0.7–2.0 eq/l, in particular 1.1–2.0 eq/l.

The separation by distillation in the reactive rectification is carried out with the aid of internals comprising trays, rotating internals, random packing and/or ordered packing.

In the case of column trays, the following types are used:
trays having holes or slits in the tray plate.
trays having necks or chimneys which are covered by bubble caps or hoods.
trays having holes covered by movable valves in the tray plate.
trays having special structures.

In columns having rotating internals, the runback is either sprayed by means of rotating funnels or is spread as a film over a heated tube wall by means of a rotor.

Columns used in the process of the invention can contain irregular beds of various packing elements. They can be made of virtually all materials, e.g. steel, stainless steel, copper, carbon, stoneware, porcelain, glass, plastics, etc., and have various shapes, e.g. spheres, rings having smooth or profiled surfaces, rings with internal struts or passages through the wall, wire mesh rings, saddles and spirals.

Packing having a regular geometry can comprise, for example, metal sheets or meshes. Examples of packing of this type are Sulzer mesh packing BX made of metal or plastic, Sulzer lamellar packing Mellapak made of sheet metal, high-performance packings such as MellapakPlus, structured packing from Sulzer (Optiflow), Montz (BSH) and Kühni (Rombopak).

The reactive rectification column in which isobutene is reacted and from which a TBA-rich stream is taken off as bottom product has from 2 to 60 theoretical plates, in particular from 3 to 50 theoretical plates. Of these, from 5 to 58 theoretical plates are located in the stripping section, from 2 to 55 theoretical plates are located in the reaction zone and from 0 to 20 theoretical plates are located in the enrichment section above the reaction zone. The feed position is below the reactive region. Water and prereacted mixture are preferably introduced at the same position.

The operating pressure of the reactive distillation column, measured at the top of the column, is from 3 to 30 bara, in particular from 4 to 12 bara. The reflux ratio is in the range from 0.5 to 40, in particular in the range from 0.9 to 20.

The hydrocarbon feed mixture can be fed together with water and optionally TBA as solubilizer into the preliminary reactors. Catalysts used are the same ones as in the reactive distillation column. The preliminary reaction is preferably carried out in 2, 3, 4 or 5 stages. This forms a mixture of TBA, water, isobutene and other hydrocarbons.

The process of the invention can be carried out using a homogeneous mixture, i.e. a mixture saturated with water, or a heterogeneous mixture.

If the process is carried out in two stages (preliminary reaction and reaction in a reactive distillation column), more water than is consumed for complete reaction of the isobutene still present can be present in the feed to the reactive distillation column. If too little water is present in the reaction mixture from the first stage, additional water should be fed into the reactive distillation column.

The process of the invention produces a distillate which preferably contains less than 700 ppm by mass, in particular less than 450 ppm by mass, very particularly preferably less than 400 ppm by mass, of isobutene. Traces of butadiene can be removed from the raffinate II obtained in this way by selective hydrogenation. This mixture can be separated by distillation into isobutane, 1-butene and a mixture of 2-butenes and n-butane or into isobutane and a mixture of linear butenes and n-butane.

In the work-up of a distillate containing less than 450 ppm by mass of isobutene, it is possible to obtain a 1-butene containing less than 1000 ppm by mass of isobutene, which is a sought-after intermediate. It is used, for example, as comonomer in the preparation of polyethylene (LLDPE or HDPE) and of ethylene-propylene copolymers. It is also used as alkylating agent and is a starting material for the preparation of 2-butanol, butene oxide, valeraldehyde.

A further use of the virtually isobutene-free raffinate II prepared according to the invention is the preparation of n-butene oligomers, in particular by the Octol process.

The hydrocarbons remaining after the linear butenes have been separated off or removed by reaction from the raffinate II can, if desired, be hydrogenated (CSP) and worked up to give isobutane and n-butane.

The bottom product comprising TBA, water and high boilers such as $C_8$-olefins can be used directly or worked up. TBA and TBA/water azeotrope or only TBA can be prepared therefrom by known methods. Low-water TBA grades can be used as fuel components.

The advantage of the process of the invention is that a high conversion of isobutene compared to conventional processes can be achieved without large reactor volumes being necessary. This is made possible only by the combined material separation and reaction in the reactive rectification.

The following examples illustrate the invention without restricting its scope, which is defined by the description and the claims.

EXAMPLES

The raffinate stream used for the experiments had the composition:

| | |
|---|---|
| n-Butane: | 8.2% |
| Isobutane: | 2.3% |
| 1-Butene: | 29.8% |
| 2-Butene (cis + trans): | 14.2% |

Isobutene: 45.5%

The isobutene content of the raffinate is typically in the range from 35 to 55%.

Example 1

According to the Invention

The preparation of tert-butanol was carried out in a plant configured as shown in FIG. 1, with firstly only reactive distillation being examined in the interests of simplicity. The diameter of the reactive rectification column was 80 mm. In the lower part of the column, 10 laboratory bubble cap trays were installed as distillative stripping section (7), and above this was the reactive part of the column (6), which was equipped over a height of 3000 mm with Katapak-SP 12 elements from Sulzer. The feed was introduced below the reaction section of the column and consisted of prereacted mixture (5) and an additional water stream (4). The stream numbers in the following table correspond to FIG. 1. Percentages are by mass. The catalyst used was Amberlyst 35. The proportion of catalyst in the reactive zone was 25% by volume.

| Stream number | Nature of stream | Mass flow [kg/h] | Composition |
|---|---|---|---|
| 5 | Output from preliminary reactor | 5.5 | 5.9% of isobutene<br>49.1% of TBA<br>5.5% of water<br>39.5% of residual $C_4$ |
| 4 | Fresh water | 0.05 | |
| 9 | Distillate | 2.2 | 403 ppm by mass of isobutene<br>1.0% of water<br>99.0% of residual $C_4$ |
| 10 | Bottom product | 3.35 | 6.8% of water<br>93.0% of TBA<br>0.1% of $C_8$ (high boilers) |

The pressure in the reactive rectification column was 7 bar. The reflux ratio was 15.

Example 2

According to the Invention

The preparation of tert-butanol was carried out in a plant configured entirely as shown in FIG. 1.

As preliminary reactors, used was made of 3 laboratory reactors containing Amberlyst 35. The reaction water was added in stages. The first reactor had a catalyst volume of 1 l and was operated with an external circulation of 3.0 kg/h at an inlet temperature of 60° C. The fresh raffinate I feed (1) had a flow of 1 kg/h, and the amount of process water was 0.08 kg/h (2). The second reactor likewise had a catalyst volume of 1 l and was operated in a single pass at an inlet temperature of 55° C. The amount of process water for the second reactor was 0.05 kg/h (2a). The third reactor had a catalyst volume of 1 l and was operated in a single pass at an inlet temperature of 55° C. The amount of process water for the third reactor was 0.043 kg/h (2b). The pressure of the plant was set to 11.6 bar at the inlet of the first reactor. To obtain sufficient product for the subsequent distillation, the product from the reactors was firstly collected and then used as feed stream to the column.

The diameter of the reactive rectification column was 80 mm. In the lower part of the column, 15 laboratory bubble cap trays were installed as distillative stripping section (7), and above this was the reactive part of the column (6), which was equipped over a height of 3000 mm with Katapak-SP 12 elements from Sulzer. The feed was introduced below the reaction section of the column and consisted of prereacted mixture (5) without an additional water stream (4). The stream numbers in the following table correspond to FIG. 1. Percentages are by mass. The catalyst used was Amberlyst 35. The proportion of catalyst in the reactive zone was 25% by volume.

| Stream number | Nature of stream | Mass flow [kg/h] | Composition |
|---|---|---|---|
| 1 | Fresh raffinate I feed | 1.0 | 45.5% of isobutene<br>54.5% of residual $C_4$ |
| 2 | Process water | 0.34 | 49.3% of TBA<br>50.7% of water |
| 4 | Additional water for column | 0 | |
| 5 | Feed to column | 5.0 collected product from the third reactor | 5.6% of isobutene<br>48.7% of TBA<br>3.8% of water<br>40.5% of residual $C_4$<br>1.4% of other components |
| 9 | Distillate | 2.04 | 343 ppm by mass of isobutene<br>1.0% of water<br>98.9% of residual $C_4$ |
| 10 | Bottom product | 2.96 | 2.8% of water<br>95.2% of TBA<br>2.0% of other components (high boilers) |

The pressure in the reactive rectification column was 7 bar, the reflux ratio was 15.

Example 3

Comparison

The preparation of tert-butanol was carried out in a plant configured as shown in FIG. 1 under the conditions of Example, except that the introduction of the water was altered and was carried out above the reaction section. The conversion achieved was poorer, as can be seen from the isobutene concentrations in the distillate (9) in the table below.

| Stream number | Nature of stream | Mass flow [kg/h] | Concentration of the component to be separated off |
|---|---|---|---|
| 5 | Output from preliminary reactor | 5.1 | 5.9% of isobutene<br>49.1% of TBA<br>5.5% of water<br>39.5% of residual $C_4$ |
| 4 | Fresh water | 0.5 | |
| 9 | Distillate | 2.05 | 0.9% of isobutene (9000 ppm)<br>1.1% of water<br>98.0% of residual $C_4$ |
| 10 | Bottom product | 3.1 | 6.9% of water<br>93.0% of TBA<br>0.1% of other components (high boilers) |

The examples demonstrate that a higher conversion of isobutene and thus a distillate having a lower isobutene content are obtained in the process of the invention in which both the isobutene-containing stream and any water are fed in below the reactive zone than in a conventional process.

The invention claimed is:

1. A process for preparing tertiary butanol comprising reacting an isobutene-containing C4-hydrocarbon stream with water over a solid acidic catalyst, wherein
   the isobutene-containing $C_4$-hydrocarbon stream and water are reacted with addition of TBA in one or more reactor/s and the mixture obtained is fed into a reactive distillation column below the reaction zone.

2. The process as claimed in claim 1, wherein
an isobutene-containing $C_4$-hydrocarbon stream, water and tert-butanol are fed into the reactive distillation column.

3. The process as claimed in claim 1, wherein
an isobutene-containing $C_4$-hydrocarbon stream is firstly reacted with water over an acidic solid catalyst to a conversion of isobutene into tert-butanol of from 65 to 97% and the mixture obtained in this way is fed into the reactive distillation column.

4. The process as claimed in claim 1, wherein
a $C_4$-hydrocarbon stream having an isobutene content of less than 700 ppm by mass is taken off at the top of the reactive distillation column.

5. The process as claimed in claim 1, wherein
the mixture obtained at the top of the reactive distillation column is separated into an aqueous phase and an organic phase and the aqueous phase is returned to the reactive distillation column.

6. The process as claimed in claim 1, wherein
the reactive distillation column is configured as a distillation column provided with one or more external reactors in which the catalyst is present and through which a secondary stream passes.

7. The process as claimed in claim 1, wherein
the reactive distillation column is configured as a distillation column provided with one or more catalyst-containing reactors integrated into the distillation section.

8. The process as claimed in claim 1, wherein
a homogeneous mixture saturated with water is fed into the reactive distillation column.

9. The process as claimed in claim 1, wherein
a heterogeneous mixture is fed into the reactive distillation column.

10. The process as claimed in claim 1, wherein
the isobutene-containing $C_4$-hydrocarbon stream and water are fed in at different points on the reactive distillation column.

* * * * *